United States Patent

Cotteret et al.

Patent Number: 5,279,619
Date of Patent: Jan. 18, 1994

[54] PROCESS FOR DYEING KERATINOUS FIBERS WITH 2,4-DIAMINO-1,3-DIMETHOXYBENZENE AT AN ACID PH AND COMPOSITIONS EMPLOYED

[75] Inventors: Jean Cotteret, Verneuil-sur-Seine; Marie P. Audousset, Levallois-Perret, both of France

[73] Assignee: L'Oreal, Paris, France

[21] Appl. No.: 110

[22] Filed: Jan. 4, 1993

Related U.S. Application Data

[63] Continuation of Ser. No. 707,869, May 31, 1991.

[30] Foreign Application Priority Data

May 31, 1990 [FR] France .................... 90 06801

[51] Int. Cl.⁵ ............................. A61K 7/13
[52] U.S. Cl. ......................... 8/406; 8/405; 8/408; 8/409; 8/410; 8/411; 8/412; 564/443; 424/70
[58] Field of Search ............ 8/405, 406, 408, 409, 8/410, 411, 412, 421; 564/443; 424/70

[56] References Cited

U.S. PATENT DOCUMENTS

| | | | |
|---|---|---|---|
| 4,566,876 | 1/1986 | Brown et al. | 8/429 |
| 4,865,619 | 9/1989 | Junino et al. | 8/410 |
| 4,960,432 | 10/1990 | Junino et al. | 8/409 |
| 4,979,961 | 12/1990 | Junino et al. | 8/410 |
| 4,985,955 | 1/1991 | Grollier et al. | 8/421 |
| 5,032,137 | 7/1991 | Junino et al. | 8/410 |
| 5,032,138 | 7/1991 | Wolfram et al. | 8/410 |

FOREIGN PATENT DOCUMENTS

0370880  5/1990  European Pat. Off. .
2615730 12/1988  France .
2615732 12/1988  France .

Primary Examiner—Paul Lieberman
Assistant Examiner—William S. Parks
Attorney, Agent, or Firm—Cushman, Darby & Cushman

[57] ABSTRACT

Process for dyeing keratinous fibres, especially human keratinous fibres such as the hair, characterised in that a composition containing, in a medium suitable for dyeing, at least 2,4-diamino-1,3-dimethoxybenzene as a coupler;
an oxidation dye precursor; and
an oxidising agent; is applied to these fibres,
the pH of the composition applied to the fibres being less than 7.

21 Claims, No Drawings

PROCESS FOR DYEING KERATINOUS FIBERS WITH 2,4-DIAMINO-1,3-DIMETHOXYBENZENE AT AN ACID PH AND COMPOSITIONS EMPLOYED

This is a continuation of application Ser. No. 07/707,869, filed May 31, 1991.

The present invention relates to a new process for dyeing keratinous fibres, especially human keratinous fibres such as the hair, employing 2,4-diamino-1,3-dimethoxybenzene in combination with oxidation bases and an oxidising agent in an acid medium, and to the compositions employed during this process.

It is known to dye keratinous fibres, and especially human hair, with dyeing compositions containing, in an alkaline medium, oxidation dye precursors and especially p-phenylenediamines or ortho- or para-aminophenols, generally referred to as "oxidation bases".

It is also known that the hues obtained with these oxidation bases may be varied by combining them with couplers, also referred to as colour modifiers, selected, in particular, from aromatic meta-diamines, meta-aminophenols and meta-diphenols.

The Applicant has already proposed 2,4-diamino-1,3-dimethoxybenzene as a coupler for dyeing in an alkaline oxidising medium.

The Applicant has just discovered that the use of this coupler with oxidation bases in a mixture, prepared at the time of use, with an oxidising agent, at an acid pH, makes it possible to obtain a colour strength at least equal to that obtained previously at an alkaline pH and an exceptional stability of the dyeing to light, washing, perspiration and adverse weather.

The subject of the present invention is hence a process for dyeing keratinous fibres, especially human keratinous fibres such as the hair, comprising the application to these fibres of at least one composition containing 2,4-diamino-1,3-dimethoxybenzene, an oxidation dye precursor, also referred to as an oxidation base, and an oxidising agent, at an acid pH.

The subject of the invention is also a dyeing agent containing two components, one of which components comprises 2,4-diamino-1,3-dimethoxybenzene and the oxidation dye precursor and the other oxidising agent at an acid pH, and in such quantities that the mixture has an acid pH.

The subject of the invention is also the ready-to-use composition containing the different agents used for dyeing the hair in an acid medium.

Other subjects of the invention will become apparent on reading the description and the examples which follow.

The process for dyeing keratinous fibres, and especially human keratinous fibres such as the hair, according to the invention, is essentially characterised in that a composition containing, in a medium suitable for dyeing, at least, as a coupler, 2,4-diamino-1,3-dimethoxybenzene, as well as the salts of this compound;
at least one oxidation dye precursor or oxidation base; and
at least one oxidising agent; is applied to these fibres, the pH of the composition applied to the fibres being less than 7.

The composition does not contain iodide ions in a sufficient quantity to oxidise the 2,4-diamino-1,3-dimethoxybenzene.

The salts are selected from the addition salts with acids such as hydrochloric and sulphuric acids, and the like.

The oxidation dye precursors or oxidation bases are known compounds which are not in themselves dyes and which form a dye by a process of oxidative condensation, either with themselves or in the presence of a coupler or modifier. These compounds generally contain an aromatic ring bearing functional groups, consisting either of two amino groups or of an amino group and a hydroxyl group, these groups being in the para or ortho position with respect to one another.

The para type oxidation dye precursors used according to the invention are selected from para-phenylenediamines, para-aminophenols and heterocyclic para precursors such as 2,5-diaminopyridine, 2-hydroxy-5-aminopyridine and 2,4,5,6-tetraaminopyrimidine.

Among para-phenylenediamines, there may be mentioned the compounds corresponding to the formula (I):

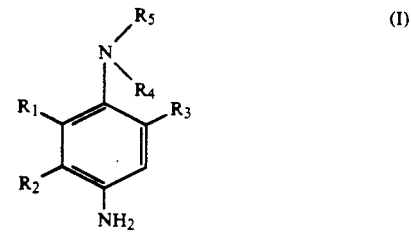

in which $R_1$, $R_2$ and $R_3$, which may be identical or different, represent a hydrogen or halogen atom, an alkyl radical having from 1 to 4 carbon atoms or an alkoxy radical having from 1 to 4 carbon atoms, and $R_4$ and $R_5$, which may be identical or different, represent a hydrogen atom or an alkyl, hydroxyalkyl, alkoxyalkyl, carbamylalkyl, mesylaminoalkyl, acetylaminoalkyl, ureidoalkyl, carbalkoxyaminoalkyl, piperidinoalkyl or morpholinoalkyl radical, these alkyl or alkoxy groups having from 1 to 4 carbon atoms, or alternatively $R_4$ and $R_5$, together with the nitrogen atom to which they are linked, form a piperidino or morpholino heterocycle, with the proviso that $R_1$ or $R_3$ represents a hydrogen atom when $R_4$ and $R_5$ do not represent a hydrogen atom, as well as the salts of these compounds, with the exception of 2,6-dimethyl-paraphenylenediamine and 2,3-dimethyl-para-phenylenediamine.

Among preferred compounds corresponding to the formula (I), there may be mentioned isopropyl-p-phenylenediamine, p-phenylenediamine, 2-methyl-p-phenylenediamine, methoxy-para-phenylenediamine, chloro-paraphenylenediamine, 2-methyl-5-methoxy-para-phenylenediamine, 2,6-dimethyl-5-methoxy-para-phenylenediamine, N,N-dimethyl-para-phenylenediamine, 3-methyl-4-amino-N,N-diethylaniline, N,N-bis(β-hydroxyethyl)para-phenylenediamine, 3-methyl-4-amino-N,N-bis(β-hydroxyethyl)aniline, 3-chloro-4-amino-N,N-bis(β-hydroxyethyl)aniline, 4-amino-N-ethyl-N-(carbamylmethyl)aniline, 3-methyl-4-amino-N-ethyl-N-(carbamylmethyl)aniline, 4-amino-N-ethyl-N-(β-piperidinoethyl)aniline, 3-methyl-4-amino-N-ethyl-N-(βpiperidinoethyl)aniline, 4-amino-N-ethyl-N-(β-morpholinoethyl)aniline, 3-methyl-4-amino-N-ethyl-N-(β-morpholinoethyl)aniline, 4-amino-N-ethyl-N-(β-acetylaminoethyl)aniline, 4-amino-N-(β-methoxyethyl- )aniline, 3-methyl-4-amino-N-ethyl-N-(β-acetylaminoethyl)aniline, 4-amino-N-ethyl-N-(β-mesylaminoethyl)aniline, 3-methyl-4-amino-N-ethyl-N-(β-mesylaminoethyl)aniline, 4-amino-N-ethyl-N-(β-sulphoethyl)aniline, 3-methyl-4-amino-N-ethyl-N-(β-sulphoethyl)aniline, N-(4-aminophenyl)morpholine and N-(4-aminophenyl)piperidine.

These para type oxidation dye precursors may be introduced into the dyeing composition either in the form of a free base or in the form of salts, for example in the form of a hydrochloride, hydrobromide or sulphate.

Among p-aminophenols, there may be mentioned p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2-hydroxymethyl-4-amino-phenol, 2-(β-hydroxyethyl)-4-aminophenol, 2-methoxy-4-aminophenol, 3-methoxy-4-aminophenol, 2,5-dimethyl-4-aminophenol and 2-methoxymethyl-4-aminophenol.

The ortho type oxidation dye precursors are selected from ortho-aminophenols such as 1-amino-2-hydroxybenzene, 6-methyl-1-hydroxy-2-aminobenzene, 4-methyl-1-amino-2-hydroxybenzene and ortho-phenylenediamines.

The oxidising agent is preferably selected from hydrogen peroxide, urea peroxide, alkali metal bromates and persalts such as perborates and persulphates. Hydrogen peroxide is especially preferred.

The pH of the composition applied to the keratinous fibres, especially the hair, has a value of less than 7 and is preferably between 3 and 6.9. This pH is adjusted by the use of acidifying agents which are well known in the field of dyeing of keratinous fibres, and especially human hair, such as inorganic or organic acids, for example hydrochloric acid, phosphoric acid, carboxylic acids such as tartaric acid and citric acid or sulphonic acids.

2,4-Diamino-1,3-dimethoxybenzene is present in the composition applied to the keratinous fibres in proportions preferably of between 0.01 and 3.5% by weight relative to the total weight of the composition.

The compositions defined above, applied in the dyeing of keratinous fibres, can also contain, in addition to 2,4-diamino-1,3-dimethoxybenzene, other couplers which are known per se, such as meta-diphenols, meta-aminophenols, meta-phenylenediamines, meta-(N-acylamino)phenols, meta-ureidophenols, meta-carbalkoxyamino phenols, α-naphthol and couplers possessing an active methylene group such as diketo compounds and pyrazolones.

Among these couplers which can be used in addition to 2,4-diamino-1,3-dimethoxybenzene, there may be mentioned 2,4-dihydroxyphenoxyethanol, 2,4-dihydroxyanisole, meta-aminophenol, resorcinol, resorcinol monomethyl ether, 2-methylresorcinol, pyrocatechol, 2-methyl-5-[N-(β-hydroxyethyl)amino]phenol, 2-methyl-5-[N-(βmesylaminoethyl)amino]phenol, 6-hydroxybenzomorpholine, 2,4-diaminoanisole, 2,4-diaminophenoxyethanol, 6-aminobenzomorpholine, 2-[N-(β-hydroxyethyl)amino]-4-aminophenoxyethanol, 2-amino-4-[N-(β-hydroxyethyl)amino]anisole, 2,4-diaminophenyl β,γ-dihydroxypropyl ether, 2,4-diaminophenoxyethylamine, 2-methyl-5-aminophenol, 2,6-dimethyl-3-aminophenol, 3,4-methylenedioxyphenol, 3,4-methylenedioxyaniline and their salts.

These compositions can also contain anionic, cationic, nonionic or amphoteric surfactants or mixtures thereof.

Among these surfactants, there may be mentioned alkylbenzenesulphonates, alkylnaphthalenesulphonates, fatty alcohol sulphates, ether sulphates and sulphonates, quaternary ammonium salts such as trimethylcetylammonium bromide and cetylpyridinium bromide, fatty acid ethanolamides, optionally oxyethylenated, polyoxyethylenated acids, alcohols or amines, polyglycerolated alcohols, polyoxyethylenated or polyglycerolated alkylphenols and also polyoxyethylenated alkyl sulphates.

The dyeing compositions are generally aqueous, but they can also contain organic solvents to solubilise compounds which might not be sufficiently water-soluble. Among these solvents, there may be mentioned, by way of example, $C_2$-$C_4$ lower alkanols such as ethanol and isopropanol, glycerol, glycols or glycol ethers such as 2-butoxyethanol, ethylene glycol, propylene glycol and diethylene glycol monoethyl ether and monomethyl ether, and also aromatic alcohols such as benzyl alcohol or phenoxyethanol, or mixtures of these solvents.

The composition applied to the hair can also contain thickening agents selected, in particular, from sodium alginate, gum arabic, cellulose derivatives such as methylcellulose, hydroxyethylcellulose, hydroxypropylcellulose, hydroxymethylcellulose and carboxymethylcellulose, acrylic acid polymers, optionally crosslinked, and xanthan gum. Inorganic thickening agents such as bentonite can also be used.

The composition can also contain antioxidants selected, in particular, from sodium sulphite, thioglycolic acid, sodium bisulphite, ascorbic acid and hydroquinone, as well as other cosmetically acceptable adjuvants when it is intended that the composition be used for dyeing human keratinous fibres, such as penetrating agents, sequestering agents, preservatives, buffers, fragrances, and the like.

The composition applied to the hair can take various forms, such as the form of liquids, creams or gels or any other form suitable for carrying out hair dyeing. It may be packaged in an aerosol can in the presence of a propellant.

The subject of the invention is also the ready-to-use composition used in the process defined above.

According to a preferred embodiment, the process comprises a preliminary step consisting in storing separately, on the one hand the composition containing, in a medium suitable for dyeing, the coupler 2,4-diamino-1,3-dimethoxybenzene and the oxidation dye precursors in the form of a component (A), and on the other hand a composition containing the oxidising agent as defined above in the form of a component (B), and in mixing them at the time of use before applying this mixture to the keratinous fibres, as described above. The component (A) does not contain iodide ions in a sufficient quantity to oxidise the 2,4-diamino-1,3-dimethoxybenzene.

The composition applied to the keratinous fibres results from a mixture of 10 to 90% of the component (A) with 90 to 10% of the component (B) containing an oxidising agent.

The subject of the invention is also an agent for dyeing keratinous fibres, especially the hair, essentially characterised in that it contains at least two components, one of the components consisting of the component (A) defined above and the other consisting of the component (B) also defined above, the pH of the components (A) and (B) being such that, after mixing in proportions of 90 to 10% for the component (A) and 10 to 90% for the component (B), the resulting composition has a pH of less than 7.

In this embodiment, the component (A), which contains at least 2,4-diamino-1,3-dimethoxybenzene and an oxidation dye precursor, has a pH of between 3 and 10.5, and may be adjusted to the chosen value by means of alkalinising agents customarily used in the dyeing of keratinous fibres, such as ammonia solution, alkali metal carbonates, alkanolamines such as mono-, di- and triethanolamines and also their derivatives, or conventional acidifying agents such as inorganic or organic acids, for example hydrochloric and phosphoric acids, carboxylic acids such as tartaric or citric acid, or sulphonic acids.

This composition can contain the various other adjuvants mentioned above, in particular couplers other than the coupler 2,4-diamino-1,3-dimethoxybenzene.

The combination of oxidation dye precursors of the para and/or ortho type as well as the couplers are present in proportions preferably of between 0.3 and 7% by weight relative to the total weight of the component (A). The concentration of 2,4-diamino-1,3-dimethoxybenzene can vary between 0.05 and 3.5% by weight relative to the total weight of the component (A).

The surfactants are present in the component (A) in proportions of 0.1 to 55% by weight. When the medium contains solvents in addition to water, they are present in proportions of between 0.5 and 40% by weight, and especially between 5 and 30% by weight, relative to the total weight of the component (A). The thickening agents are preferably present in proportions of between 0.1 and 5%, and especially between 0.2 and 3%, by weight. The antioxidants mentioned above are preferably present in the component (A) in proportions of between 0.02 and 1.5% by weight relative to the total weight of the component (A).

The component (B) containing the oxidising agent as defined above has a pH of less than 7. This pH can have a minimum value of 1, and is preferably between 1.5 and 3.5. This component (B) may be acidified with the same type of acidifying agents as those used for the component (A).

It can take the form of a liquid, more or less thickened, milk or gel.

This two-component dyeing agent may be packaged in a multi-compartment device or dyeing kit, or any other multi-compartment packaging system in which one compartment contains the component (A) and the second contains the component (B); it being possible for these devices to be equipped with a means enabling the desired mixture to be delivered on the hair, such as the device described in the Applicant's U.S. Pat. No. 4,823,985.

The subject of the invention is also the use as a coupler of 2,4-diamino-1,3-dimethoxybenzene for dyeing keratinous fibres in an acid medium, in combination with oxidation dye precursors.

According to the invention, the dyeing process consists in applying the mixture obtained to the hair, in leaving it in place for 3 to 40 minutes and then in rinsing the hair and optionally shampooing.

It is also possible, according to the invention, to apply separately a composition containing the coupler 2,4-diamino-1,3-dimethoxybenzene, the oxidation dye precursor and the oxidising agent, so that the mixture formed in situ on the fibres has a pH of less than 7, as defined above.

The examples which follow are intended as illustrations of the invention, no limitation being implied.

EXAMPLES 1 to 5

Hair dyeing is performed by applying a mixture, prepared at the time of use, of the dyeing composition (A) and the oxidising composition (B) to permanent-waved grey hair which is 90% white.

This mixture has the pH shown in the table of examples which follow.

This mixture is left to act for 30 minutes and the hair is then rinsed and shampooed.

After drying, the hair is dyed in the hue specified at the bottom of the table.

| in g | 1 | 2 | 3 | 4 | 5 |
|---|---|---|---|---|---|
| A) Dyeing composition | | | | | |
| 2,4-Diamino-1,3-dimethoxybenzene. 2 HCl | 0.723 | 0.482 | 0.241 | 0.723 | 0.723 |
| para-Phenylenediamine | 0.324 | | | 0.324 | |
| para-Aminophenol | | 0.436 | | | |
| 2-Methyl-para-phenylenediamine. 2 HCl | | | 0.488 | | 0.555 |
| 2-Methyl-5-[N-(β-hydroxyethyl)amino]phenol | | 0.334 | | | |
| meta-Aminophenol | | | 0.144 | | |
| α-Naphthol | | | 0.109 | | |
| Monoethanolamine qs pH | 9.8 | 9.7 | 9.1 | 9.0 | 8.7 |
| Vehicle 1 | X | X | | | |
| Vehicle 2 | | | X | X | X |
| Water qs | 100 | 100 | 100 | 100 | 100 |
| B) Oxidising composition | | | | | |
| Hydrogen peroxide solution, "20 volumes" | | | | | |
| Phosphoric acid qs pH | 1.1 | 1.4 | 1.2 | 1.2 | 1.2 |
| pH w/w mixture A + B | 5.5 | | 6.5 | 6.4 | 6 |
| pH mixture ⅓ A + ⅔ B | | 4.8 | | | |
| Hues obtained: | intense midnight blue | pink | intense blue | intense blue | intense blue |

EXAMPLE 6

| 2,4-Diamino-1,3-dimethoxybenzene | 0.1 g |

| -continued | | |
|---|---|---|
| para-Phenylenediamine | | 0.4 g |
| meta-Aminophenol | | 0.3 g |
| Cetyl/stearyl alcohol | | 18.0 g |
| 2-Octyldodecanol | | 3.0 g |
| Oxyethylenated cetyl/stearyl alcohol containing 15 moles of ethylene oxide | | 3.0 g |
| Ammonium lauryl sulphate | | 3.6 g |
| Monoethanolamine | | 3.0 g |
| Sequestering agent, antioxidant | qs | qs |
| Water | qs | 100.0 g |

The pH of this composition is equal to 10.2.

At the time of use, the above composition is mixed, weight for weight, with "20 volumes" hydrogen peroxide solution, the pH of which is adjusted to between 1 and 1.5 (by adding 2.5 g of phosphoric acid to 100 g of hydrogen peroxide solution).

The pH of the compsition after mixing is equal to 6.8. This mixture is applied to grey hair which is 90% white for 30 minutes.

After rinsing, washing and drying, the hair is dyed ash brown.

| DYEING VEHICLE 1 | |
|---|---|
| Nonylphenol containing 4 moles of ethylene oxide, sold by the company HENKEL under the name "SINNOPAL NP4" | 25.5 g |
| Nonylphenol containing 9 moles of ethylene oxide, sold by the company HENKEL under the name "SINNOPAL NP9" | 17.5 g |
| Ethylene glycol monoethyl ether | 7.0 g |
| Propylene glycol | 10.5 g |
| Dipropylene glycol | 0.5 g |
| Ethyl alcohol | 2.0 g |
| Monoethanolamine lauryl ether sulphate sold by the company LEVER at a concentration of 28% AS under the name "SACTIPON 2 OM 29" | 4.2 g AS |
| Sodium alkyl ether sulphate containing 28% AS | 0.8 g AS |
| Sodium metabisulphite in aqueous solution containing 35% AS | 0.45 g AS |
| Sodium acetate | 0.8 g |
| Antioxidant, sequestering agent | qs |

| DYEING VEHICLE 2 | |
|---|---|
| Polyglycerolated oleyl alcohol containing 2 moles of glycerol | 4.0 g |
| Polyglycerolated oleyl alcohol containing 4 moles of glycerol at a concentration of 78% AS | 5.69 g AS |
| Oleic acid | 3.0 g |
| Oleylamine containing 2 moles of ethylene oxide, sold by the company AKZO under the name "ETHOMEEN O 12" | 7.0 g |
| Diethylaminopropyl laurylamino-succinimate sodium salt containing 55% AS | 3.0 g AS |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite in aqueous solution containing 35% AS | 0.45 g AS |
| Ammonium acetate | 0.8 g |
| Antioxidant, sequestering agent | qs |

We claim:

1. A one-step process for dyeing keratinous fibers consists of applying to said fibers in an amount effective to dye said fibers an acid composition comprising, in a medium suitable for dyeing said fibers, a mixture of:
   (i) 2,4-diamino-1,3-dimethoxybenzene, as a coupler, in an amount ranging from 0.01 to 3.5 percent by weight based on the total weight of said composition;
   (ii) at least one óxidation dye precursor;
   (iii) at least one oxidizing agent, present in an amount effective to oxidize said coupler and said oxidation dye precursor; and
   (iv) an acid component present in an amount sufficient such that said mixture has a pH less than 7,
   said composition not containing iodide ions in an amount sufficient to oxidize said 2,4-diamino-1,3-dimethoxybenzene and said oxidation dye precursor.

2. The one-step process of claim 1 wherein said oxidation dye precursor is selected from the group consisting of a paraphenylenediamine, a para-aminophenol and a heterocyclic para precursor.

3. The one-step process of claim 2 wherein said paraphenylenediamine has the formula

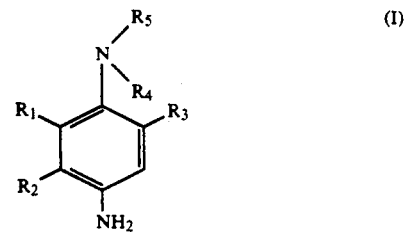

wherein
   $R_1$, $R_2$ and $R_3$, each independently, represent hydrogen, halogen, alkyl having 1–4 carbon atoms or alkoxy having 1–4 carbon atoms,
   $R_4$ and $R_5$, each independently, represent hydrogen, alkyl, hydroxyalkyl, alkoxyalkyl, carbamylalkyl, mesylaminoalkyl, acetylaminoalkyl, ureidoalkyl, carbalkoxyaminoalkyl, piperidinoalkyl or morpholinoalkyl, wherein the alkyl or alkoxy moieties have from 1 to 4 carbon atoms, or
   $R_4$ and $R_5$, together with the nitrogen atom to which they are attached, form a piperidino or morpholino heterocycle,
   with the proviso that $R_1$ or $R_3$ represents hydrogen when $R_4$ and $R_5$ do not represent hydrogen,
   and a salt of said paraphenylenediamine,
   with the exception of 2,6-dimethylparaphenylenediamine and 2,3-dimethylparaphenylenediamine.

4. The one-step process of claim 3 wherein said paraphenylenediamine of formula (I) is selected from the group consisting of
   isopropyl-p-phenylenediamine,
   p-phenylenediamine,
   2-methyl-p-phenylenediamine,
   methoxy-paraphenylenediamine,
   chloro-para-phenylenediamine,
   2-methyl-5-methoxy-para-phenylenediamine,
   2,6-dimethyl-5-methoxy-para-phenylenediamine,
   N,N-dimethyl-para-phenylenediamine,
   3-methyl-4-amino-N,N-diethylaniline,
   N,N-bis(β-hydroxyethyl) para-phenylenediamine,
   3-methyl-4-amino-N,N-bis (β-hydroxyethyl) aniline, 3-chloro-4-amino-N,N-bis (β-hydroxyethyl) aniline,
4-amino-N-ethyl-N-(carbamylmethyl) aniline,
3-methyl-4-amino-N-ethyl-N-(carbamylmethyl) aniline,
4-amino-N-ethyl-N-(β-piperidinoethyl) aniline,
3-methyl-4-amino-N-ethyl-N-(β-piperidinoethyl) aniline,
4-amino-N-ethyl-N-(β-morpholinoethyl) aniline,
3-methyl-4-amino-N-ethyl-N-(β-morpholinoethyl) aniline,
4-amino-N-ethyl-N-(β-acetylaminoethyl) aniline,
4-amino-N-(β-methoxyethyl) aniline,
3-methyl-4-amino-N-ethyl-N-(β-acetylaminoethyl) aniline,
4-amino-N-ethyl-N-(β-mesylaminoethyl) aniline,
3-methyl-4-amino-N-ethyl-N-(β-mesylaminoethyl) aniline,
4-amino-N-ethyl-N-(β-sulphoethyl) aniline,
3-methyl-4-amino-N-ethyl-N-(β-sulphoethyl) aniline,
N-(4-aminophenyl) morpholine and
N-(4-aminophenyl) piperidine,
in the form of a free base or a salt.

5. The one-step process of claim 2 wherein said para-aminophenol is selected from the group consisting of
para-aminophenol,
2-methyl-4-aminophenol,
3-methyl-4-aminophenol,
2-chloro-4-aminophenol,
3-chloro-4-aminophenol,
2,6-dimethyl-4-aminophenol,
3,5-dimethyl-4-aminophenol,
2,3-dimethyl-4-aminophenol,
2-hydroxymethyl-4-aminophenol,
2-(β-hydroxyethyl)-4-aminophenol,
2-methoxy-4-aminophenol,
3-methoxy-4-aminophenol,
2,5-dimethyl-4-aminophenol and
2-methoxymethyl-4-aminophenol.

6. The one-step process of claim 1 wherein said oxidation dye precursor is an ortho type oxidation dye precursor selected from the group consisting of an ortho-aminophenol and an ortho-phenylenediamine.

7. The one-step process of claim 1 wherein said oxidizing agent is selected from the group consisting of hydrogen peroxide, urea peroxide, an alkali metal bromate and a persalt.

8. The one-step process of claim 1 wherein said composition has a pH ranging from 3 to 6.9.

9. The one-step process of claim 1 wherein said composition contains, in addition to said 2,4-diamino-1,3-dimethoxybenzene, at least one other coupler selected from the group consisting of a meta-diphenol, a meta-aminophenol, a meta-phenylenediamine, a meta-(N-acylamino) phenol, a meta-ureidophenol, a meta-carbalkoxyaminophenol, α-naphthol and a coupler possessing an active methylene group selected from a diketo compound and a pyrazolone.

10. The one-step process of claim 9 wherein said other coupler is selected from the group consisting of
2,4-dihydroxyphenoxyethanol,
2,4-dihydroxyanisole,
meta-aminophenol,
resorcinol,
resorcinol monomethyl ether,
2-methylresorcinol,
pyrocatechol,
2-methyl-5-[N-(β-hydroxyethyl)amino] phenol,
2-methyl-5-[N-(β-mesylaminoethyl) amino] phenol,
6-hydroxybenzomorpholine,
2,4-diaminoanisole,
2,4-diaminophenoxyethanol,
6-aminobenzomorpholine,
2-[N-(β-hydroxyethyl)-amino]-4-aminophenoxyethanol,
2-amino-4-[N-(β-hydroxyethyl) amino] anisole,
2,4-diaminophenyl β,γ-dihydroxypropyl ether,
2,4-diaminophenoxyethylamine,
2-methyl-5-aminophenol,
2,6-dimethyl-3-aminophenol,
3,4-methylenedioxyphenol,
3,4-methylenedioxyaniline, or a salt thereof.

11. The one-step process of claim 1 wherein said composition also contains at least one of an anionic, cationic, nonionic or amphoteric surfactant or a mixture thereof; a thickening agent; or an antioxidant.

12. The one-step process of claim 1 wherein said medium suitable for dyeing said keratinous fibers is water or a mixture of water and a solvent selected from the group consisting of a $C_2$–$C_4$ lower alkanol, glycerol, a glycol, a glycol ether, diethylene glycol monoethylether, diethylene glycol monomethylether, an aromatic alcohol; and a mixture thereof.

13. The one-step process of claim 1 wherein said composition is permitted to remain in contact with said fibers for a period of time ranging from 3 to 40 minutes.

14. The one-step process of claim 13 wherein subsequently the thus dyed hair is rinsed, optionally shampooed and rinsed again, and dried.

15. An agent for dyeing keratinous fibers consisting essentially of at least two components, one of said components, component (A), comprising in an aqueous medium suitable for dyeing said fibers, 2,4-diamino-1,3-dimethoxybenzene, as a coupler, in an amount ranging from 0.05 to 3.5 percent by weight based on the total weight of said component (A); and an oxidation dye precursor selected from the group consisting of a para-phenylenediamine, a para-aminophenol and a heterocyclic para precursor, said component (A) not containing iodide ions in an amount sufficient to oxidize said 2,4-diamino-1,3-dimethoxybenzene and another of said components, component (B), comprising in an aqueous medium, suitable for dyeing said fibers, an oxidizing agent present in an amount effective to oxidize said 2,4-diamino-1,3-dimethoxybenzene and said oxidation dye precursor and an acid component in an amount sufficient such that a mixture of 90 to 10 weight percent of component (A) and 10 to 90 weight percent of component (B) has a pH of less than 7.

16. The agent of claim 15, wherein said component (A) has a pH ranging from 3 to 10.5.

17. The agent of claim 15 wherein said oxidation dye precursor is present in an amount ranging from 0.3 to 7 percent by weight based on the total weight of said component (A).

18. The agent of claim 15 wherein said 2,4-diamino-1,3-dimethoxybenzene is present in an amount ranging from 0.05 to 3.5 percent by weight based on the total weight of said component (A).

19. The agent of claim 15 wherein said component (B) has a pH ranging from 1 to less than 7.

20. A multi-compartment kit for dyeing keratinous fibers comprising a first compartment containing a component (A) comprising in a medium suitable for dyeing said fibers, 2,4-diamino-1,3-dimethoxybenzene, as a coupler; and an oxidation dye precursor selected from the group consisting of a para-phenylenediamine, a para-aminophenol and a heterocyclic para precursor; and a second compartment containing a component (B) comprising, in an aqueous medium suitable for dyeing said fibers, an oxidizing agent present in an amount sufficient to oxidize said 2,4-diamino-1,3-dimethoxybenzene and said oxidation dye precursor and an acid component in an amount sufficient such that the pH of a composition resulting from the admixture of from 90 to 10 percent by weight of component (A) with 10 to 90 percent by weight of component (B) is less than 7.

21. An agent for dyeing keratinous fibers consisting essentially of at least two components, one of said components, component (A), comprising in a medium suitable for dyeing said fibers, at least 2,4-diamino-1,3-dimethoxybenzene, as a coupler and present in an amount ranging from 0.05 to 3.5 percent by weight based on the total weight of said component (A); and an oxidation dye precursor selected from the group consisting of a para-phenylenediamine, a para-aminophenol and a heterocyclic para precursor, the combination of said oxidation dye precursor and said coupler being present in an amount ranging from 0.3 to 7 percent by weight relative to the total weight of said component (A), said component (A) not containing iodide ions in an amount sufficient to oxidize said 2,4-diamino-1,3-dimethoxybenzene and said oxidation dye precursor, and another of said components, component (B), comprising, in an aqueous medium suitable for dyeing said fibers, an oxidizing agent present in an amount sufficient to oxidize said coupler and said oxidation dye precursor and an acid component in an amount sufficient such that the pH of a composition resulting from the admixture of from 90 to 10 percent by weight of component (A) with 10 to 90 percent by weight of component (B) is less than 7.

* * * * *